(12) United States Patent
Sussillo et al.

(10) Patent No.: US 11,461,618 B2
(45) Date of Patent: *Oct. 4, 2022

(54) MULTIPLICATIVE RECURRENT NEURAL NETWORK FOR FAST AND ROBUST INTRACORTICAL BRAIN MACHINE INTERFACE DECODERS

(71) Applicant: The Board of Trustees of the Leland Stanford Junior University, Stanford, CA (US)

(72) Inventors: David Sussillo, Portola Valley, CA (US); Jonathan C. Kao, Stanford, CA (US); Sergey Stavisky, San Francisco, CA (US); Krishna V. Shenoy, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 884 days.

This patent is subject to a terminal disclaimer.

(21) Appl. No.: 16/292,000

(22) Filed: Mar. 4, 2019

(65) Prior Publication Data
US 2019/0205731 A1 Jul. 4, 2019

Related U.S. Application Data

(63) Continuation of application No. 14/826,300, filed on Aug. 14, 2015, now Pat. No. 10,223,634.
(Continued)

(51) Int. Cl.
*G06N 3/04* (2006.01)
*G06N 3/08* (2006.01)
*A61B 5/24* (2021.01)

(52) U.S. Cl.
CPC .............. *G06N 3/0445* (2013.01); *A61B 5/24* (2021.01); *G06N 3/04* (2013.01); *G06N 3/08* (2013.01)

(58) Field of Classification Search
CPC .......... G06N 3/04; G06N 3/0445; G06N 3/08; A61B 5/04001; A61B 5/24; G05B 13/027;
(Continued)

(56) References Cited

U.S. PATENT DOCUMENTS 8,335,993 B1 12/2012 Tan
D684,154 S 6/2013 Schontag
(Continued)

FOREIGN PATENT DOCUMENTS

KR 20130002590 A 1/2013
KR 20150133937 A 12/2015
WO 2022006462 A1 1/2022

OTHER PUBLICATIONS

Sussillo et al., "Making brain-machine interfaces robust to future neural variability", Nature Communications, Published Dec. 13, 2016. (Date precludes usage). (Previously supplied). (Year: 2016).*
(Continued)

*Primary Examiner* — Dave Misir
(74) *Attorney, Agent, or Firm* — KPPB LLP

(57) ABSTRACT

A brain machine interface (BMI) to control a device is provided. The BMI has a neural decoder, which is a neural to kinematic mapping function with neural signals as input to the neural decoder and kinematics to control the device as output of the neural decoder. The neural decoder is based on a continuous-time multiplicative recurrent neural network, which has been trained as a neural to kinematic mapping function. An advantage of the invention is the robustness of the decoder to perturbations in the neural data; its perfor-
(Continued)

mance degrades less—or not at all in some circumstances—in comparison to the current state decoders. These perturbations make the current use of BMI in a clinical setting extremely challenging. This invention helps to ameliorate this problem. The robustness of the neural decoder does not come at the cost of some performance, in fact an improvement in performance is observed.

14 Claims, 6 Drawing Sheets

Related U.S. Application Data

(60) Provisional application No. 62/037,441, filed on Aug. 14, 2014.

(58) Field of Classification Search
CPC .......... G05B 2219/33025; G05B 2219/33027; G05B 2219/23067
USPC ........................................................ 706/23
See application file for complete search history.

(56) References Cited

U.S. PATENT DOCUMENTS

| | | | |
|---|---|---|---|
| 8,949,743 B2 | 2/2015 | Kida et al. | |
| 9,373,088 B2 | 6/2016 | Nuyujukian et al. | |
| 10,223,634 B2 | 3/2019 | Sussillo et al. | |
| 10,779,746 B2 | 9/2020 | Even-Chen et al. | |
| 10,949,086 B2 | 3/2021 | Even-Chen et al. | |
| 2003/0056278 A1 | 3/2003 | Kuo et al. | |
| 2003/0105409 A1 | 6/2003 | Donoghue et al. | |
| 2004/0073414 A1 | 4/2004 | Bienenstock et al. | |
| 2004/0267320 A1* | 12/2004 | Taylor ................ | A61F 2/72 607/2 |
| 2005/0017870 A1 | 1/2005 | Allison et al. | |
| 2005/0228515 A1 | 10/2005 | Musallam et al. | |
| 2006/0159195 A1 | 7/2006 | Ionescu et al. | |
| 2006/0167371 A1 | 7/2006 | Flaherty et al. | |
| 2006/0274060 A1 | 12/2006 | Ni et al. | |
| 2009/0167706 A1 | 7/2009 | Tan et al. | |
| 2010/0241993 A1 | 9/2010 | Chae | |
| 2010/0274746 A1* | 10/2010 | Rickert .............. | G06K 9/00536 706/14 |
| 2010/0280403 A1 | 11/2010 | Erdogmus et al. | |
| 2011/0092842 A1 | 4/2011 | Decaria et al. | |
| 2011/0224572 A1* | 9/2011 | Gilja ................ | A61F 2/72 600/545 |
| 2011/0295143 A1 | 12/2011 | Leuthardt et al. | |
| 2011/0307079 A1 | 12/2011 | Oweiss et al. | |
| 2012/0022391 A1 | 1/2012 | Leuthardt | |
| 2012/0030696 A1 | 2/2012 | Smith | |
| 2012/0130266 A1 | 5/2012 | Mathan et al. | |
| 2012/0221075 A1 | 8/2012 | Bentwich | |
| 2012/0242659 A1 | 9/2012 | Sun | |
| 2013/0253299 A1 | 9/2013 | Weber et al. | |
| 2013/0311412 A1* | 11/2013 | Lazar ................ | H03M 1/82 706/16 |
| 2013/0314320 A1 | 11/2013 | Hwang et al. | |
| 2014/0132519 A1 | 5/2014 | Chun | |
| 2014/0194720 A1 | 7/2014 | Hua | |
| 2014/0358192 A1 | 12/2014 | Wheeler Moss et al. | |
| 2015/0091791 A1 | 4/2015 | Segal | |
| 2015/0120777 A1 | 4/2015 | Ramos | |
| 2015/0124063 A1 | 5/2015 | Woods | |
| 2015/0248234 A1 | 9/2015 | Chen et al. | |
| 2015/0268814 A1 | 9/2015 | Wang | |
| 2015/0269336 A1 | 9/2015 | Duan et al. | |
| 2015/0297106 A1 | 10/2015 | Pasley et al. | |
| 2016/0048753 A1 | 2/2016 | Sussillo et al. | |
| 2016/0180215 A1 | 6/2016 | Vinyals et al. | |
| 2016/0224891 A1 | 8/2016 | Kao et al. | |
| 2016/0299568 A1 | 10/2016 | Segal | |
| 2017/0042440 A1 | 2/2017 | Even-chen et al. | |
| 2017/0108926 A1 | 4/2017 | Moon et al. | |
| 2017/0139587 A1 | 5/2017 | Bostick et al. | |
| 2017/0147077 A1 | 5/2017 | Park et al. | |
| 2017/0344220 A1 | 11/2017 | Cook et al. | |
| 2018/0101239 A1 | 4/2018 | Yin et al. | |
| 2019/0021663 A1 | 1/2019 | Kesinger et al. | |
| 2019/0025917 A1 | 1/2019 | Francis et al. | |
| 2019/0053725 A1 | 2/2019 | Von Novak et al. | |
| 2019/0333505 A1 | 10/2019 | Stavisky et al. | |
| 2020/0057964 A1 | 2/2020 | Howard | |
| 2020/0133486 A1 | 4/2020 | Even-Chen et al. | |
| 2020/0187841 A1 | 6/2020 | Ayyad | |
| 2021/0064135 A1 | 3/2021 | Shenoy et al. | |

OTHER PUBLICATIONS

Sussillo et al., "A recurrent neural network for closed-loop intracortical brain-machine interface decoders", Journal of Neural Engineering, Published Mar. 19, 2012. (Previously supplied). (Year: 2012).*

Sutskever, "Generating Text with Recurrent Neural Networks", Proceedings of the 28th International Conference on Machine Learning, Bellevue,WA, USA, 2011 (In applicants' IDS). (Year: 2011).*

Andersen et al., "Selecting the Signals for a Brain-Machine Interface", Current Opinion in Neurobiology, vol. 14, No. 6, Dec. 2004, pp. 720-726.

Anumanchipalli et al., "Intelligible Speech Synthesis from Neural Decoding of Spoken Sentences", bioRxiv, Nov. 29, 2018, 32 pgs.

Artusi et al., "Performance of a Simulated Adaptive BCI Based on Experimental Classification of Movement-Related and Error Potentials", IEEE Journal on Emerging and Selected Topics in Circuits and Systems, vol. 1, No. 4, Dec. 2011, 9 pgs.

Bacher et al., "Neural Point-and-Click Communication by a Person With Incomplete Locked-In Syndrome", Neurorehabilitation and Neural Repair, vol. 29, No. 5, Nov. 10, 2014, pp. 462-471.

Bouchard et al., "Control of Spoken Vowel Acoustics and the Influence of Phoentic Context in Human Speech Sensorimotor Cortex", The Journal of Neuroscience, vol. 34, No. 38, Sep. 17, 2014, pp. 12662-12677.

Bouchard et al., "Functional Organization of Human Sensorimotor Cortex for Speech Articulation", HHS Public Access—Author Manuscript, 21 pgs., published in final form as Nature, vol. 495, No. 7441, Mar. 21, 2013, pp. 327-332.

Bouchard et al., "Neural Decoding of Spoken Vowels from Human Sensory-Motor Cortex with High-Density Electrocorticography", 36th Annual International Conference of the IEEE Engineering in Medicine and Biology Society, Aug. 26-30, 2014, Chicago, IL, 4 pgs.

Breshears et al., "A Probabilistic Map of the Human Ventral Sensorimotor Cortex Using Electrical Stimulation", Journal of Neurosurgery, vol. 123, No. 2, Aug. 2015, E Publication May 15, 2015, 10 pgs.

Brumberg et al., "Classification of Intended Phoneme Production from Chronic Intracortical Microelectrode Recordings in Speech-Motor Cortex", Frontiers in Neuroscience, vol. 5, May 12, 2011, 12 pgs.

Chakrabarti et al., "Progress in Speech Decoding from the Electrocorticogram", Biomedical Engineering Letters, vol. 5, No. 1, Mar. 2015, pp. 10-21.

Chan et al., "Decoding Word and Category-Specific Spatiotemporal Representations from MEG and EEG", NIH Public Access—Author Manuscript, 24 pgs., published in final form as Neuroimage, vol. 54, No. 4, Feb. 14, 2011, pp. 3028-3039.

Chan et al., "Speech-Specific Tuning of Neurons in Human Superior Temporal Gyrus", Cerebral Cortex, vol. 24, No. 10, Oct. 2014, pp. 2679-2693.

Chavarriaga et al., "Errare machinale est: the use of error-related potentials in brain-machine interfaces", Frontiers in Neuroscience, vol. 8, Article 208 (2014), 13 pgs.

Chestek et al., "Long-term stability of neural prosthetic control signals from silicon cortical arrays in rhesus macaque motor cortex", Journal of neural engineering, 8(4):045005, Jul. 2011, 11 pgs.

(56) References Cited

OTHER PUBLICATIONS

Cheung et al., "The Auditory Representation of Speech Sounds in Human Motor Cortex", eLife, Mar. 4, 2016, 19 pgs.
Churchland et al., "Techniques for Extracting Single-Trial Activity Patterns from Large-Scale Neural Recordings", NIH Public Access—Author Manuscript, 16 pgs., published in final form as Current Opinion in Neurobiology, vol. 17, No. 5, Oct. 2007, pp. 609-618.
Collinger et al., "7 degree-of-freedom neuroprosthetic control by an individual with tetraplegia", NIH Public Access—Author Manuscript, 17 pgs., published in final form as "High-Performance Neuroprosthetic Control by an Individual with Tetraplegia", The Lancet, vol. 381, No. 9866, Feb. 16, 2013, 17 pgs.
Creutzfeldt et al., "Neuronal Activity in the Human Lateral Temporal Lobe: I. Responses to Speech", Experimental Brain Research, vol. 77, No. 3, 1989, pp. 451-475.
Cunningham et al., "A closed-loop human simulator for investigating the role of feedback control in brain-machine interfaces", Journal of neurophysiology, 105(4):1932-1949, Apr. 2011.
Daffau et al., "The Role of Dominant Premotor Cortex in Language: A Study Using Intraoperative Functional Mapping in Awake Patients", Neuroimage, vol. 20, No. 4, Dec. 2003, pp. 1903-1914.
Einevoll et al., "Modelling and Analysis of Local Field Potentials for Studying the Function of Cortical Circuits", Nature Review Neuroscience, vol. 14, No. 11, Nov. 2013, pp. 770-785.
Even-Chen et al., "Auto-Deleting Brain Machine Interface: Error Detection Using Spiking Neural Activity in the Motor Cortex", 37th Annual International Conference of the IEEE Engineering in Medicine and Biology Society, Aug. 25-29, 2015, Milan, Italy, 5 pgs.
Even-Chen et al., "Feasibility of Automatic Error Detect-and-Undo System in Human Intracortical Brain-Computer Interfaces", IEEE Transactions on Biomedical Engineering, vol. 65, No. 8, Aug. 2018, pp. 1771-1784.
Fan et al., "Intention Estimation in Brain-Machine Interfaces", NIH Public Access—Author Manuscript, 28 pgs., published in final form as Journal Neural Engineering, vol. 11, No. 1, Feb. 2014.
Ferrez et al., "EEG-Based Brain-Computer Interaction: Improved Accuracy by Automatic Single-Trial Error Detection", Advances in Neural Information Processing Systems 20, 2007, 8 pgs.
Ferrez et al., "Simultaneous Real-Time Detection of Motor Imagery and Error-Related Potentials for Improved BCI Accuracy", In proceedings of the 4th Inti. Brain-Computer Interface Workshop and Training Course (2008), 6 pgs.
Gilja et al., "A High-Performance Neural Prosthesis Enabled by Control Algorithm Design", Nature Neuroscience, vol. 15, No. 12, Dec. 2012, Published Online: Nov. 18, 2012, pp. 1752-1757.
Golub et al., "Internal Models Engaged by Brain-Computer Interface Control", NIH Public Access—Author Manuscript, 11 pgs., published in final form as 34th Annual International Conference of the IEEE EMBS, vol. 2012, 2012, pp. 1327-1330.
Guenther et al., "A Wireless Brain-Machine Interface for Real-Time Speech Synthesis", PLoS One, vol. 4, No. 12, Dec. 9, 2009, 11 pgs.
Herff et al., "Automatic Speech Recognition from Neural Signals: A Focused Review", Front Neuroscience, vol. 10, No. 429, Sep. 2016, pp. 1-7.
Herff et al., "Brain-to-text: decoding spoken phrases from phone representations in the brain", Frontiers in Neuroscience, vol. 9, No. 217, Jun. 12, 2015, 11 pgs.
Hochberg et al., "Neuronal ensemble control of prosthetic devices by a human with tetraplegia", Nature, vol. 442, No. 7099, Jul. 13, 2006, pp. 164-171.
Homer et al., "Sensors and Decoding for Intracortical Brain Computer Interfaces", Annual Review of Biomedical Engineering, vol. 15, Jul. 2013, 25 pgs.
Jozefowicz et al., "Exploring the Limits of Language Modeling", arXiv:1602.02410v2, Feb. 11, 2016, 11 pgs.
Kao et al., "Information Systems Opportunities in Brain-Machine Interface Decoders", Proceedings of the IEEE, vol. 102, No. 5, May 2014, 17 pgs.
Kellis et al., "Decoding Spoken Words Using Local Field Potentials Recorded from the Cortical Surface", NIH Public Access—Author Manuscript, 20 pgs., published in final form as Journal of Neural Engineering, vol. 7, No. 5, Oct. 2010.
Kim et al., "Neural control of computer cursor velocity by decoding motor cortical spiking activity in humans with tetraplegia", Journal of neural engineering, 5(4):455-476, Dec. 2008.
Leuthardt et al., "Using the Electrocorticographic Speech Network to Control a Brain-Computer Interface in Humans", NIH Public Access—Author Manuscript, 22 pgs., published in final form as Journal of Neural Engineering, vol. 8, No. 3, Jun. 2011.
Lotte et al., "Electrocorticographic Representations of Segmental Features in Continuous Speech", Frontiers in Human Neuroscience, vol. 9, Feb. 24, 2015, 13 pgs.
Malik et al., "Efficient Decoding with Stead-State Kalman Filter in Neural Interface Systems", NIH Public Access—Author Manuscript, 25 pgs., published in final form as IEEE Trans Neural System Rehabilitation Engineering, vol. 19, No. 1, Feb. 2011, pp. 25-34.
Martin et al., "Decoding Spectrotemporal Features of Overt and Covert Speech from the Human Cortex", Front Neuroengineering, vol. 7, May 27, 2014, 15 pgs.
Meister et al., "Motor Cortex Hand Area and Speech: Implications for the Development of Language", Neuopsychologia, vol. 41, No. 4, 2003, pp. 401-406.
Mugler et al., "Direct Classification of all American English Phonemes Using Signals from Functional Speech Motor Cortex", NIH Public Access—Author Manuscript, 16 pgs., published in final form as Journal of Neural Engineering, vol. 11, No. 3, Jun. 2014.
Mulliken et al., "Decoding Trajectories from Posterior Parietal Cortex Ensembles", Journal of Neuroscience, vol. 28, No. 48, Nov. 26, 2008, pp. 12913-12926.
Nguyen et al., "Inferring Imagined Speech using EEG Signals: A New Approach Using Riemannian Manifold Features", Journal of Neural Engineering, vol. 15, No. 1, 2017, 16 pgs.
Nuyujukian et al., "A High-Performance Keyboard Neural Prosthesis Enabled by Task Optimization", IEEE Transactions on Biomedical Engineering, vol. 62, No. 1, Sep. 4, 2014, 9 pgs.
Nuyujukian et al., "Monkey Models for Brain-Machine Interfaces: The Need for Maintaining Diversity", 33rd Annual International Conference of the IEEE EMBS, Aug. 30- Sep. 3, 2011, Boston, Massachusetts, 5 pgs.
Orsborn et al., "Closed-Loop Decoder Adaptation Shapes Neural Plasticity for Skillful Neuroprosthetic Control", Neuron, vol. 82, No. 6, Jun. 2014, pp. 1380-1393.
Pandarinath et al., "High performance communication by people with paralysis using an intracortical brain-computer interface", Elife, vol. 6, Feb. 21, 2017, 27 pgs.
Ramsey et al., "Decoding Spoken Phonemes from Sensorimotor Cortex with High-Density ECoG Grids", Neuroimage, Oct. 15, 2018, E Publication Oct. 7, 2017, 11 pgs.
Ryu et al., "Human cortical prostheses: lost in translation?", Neurosurgical Focus, 2009, 11 pgs.
Sahin et al., "Sequential Processing of Lexical, Grammatical, and Phonological Information within Broca's Area", NIH Public Access—Author Manuscript, 11 pgs., published in final form as Science, vol. 326, No. 5951, Oct. 16, 2009, pp. 445-449.
Santhanam et al., "A high-performance brain-computer interface", Nature, vol. 442, No. 7099, Jul. 13, 2006, pp. 195-198.
Schmidt et al., "Online detection of error-related potentials boosts the performance of mental typewriters", BMC Neurosci. 13:19 (2012), 13 pgs.
Shadmehr et al., "Error Correction, Sensory Prediction, and Adaptation in Motor Control", Annu Rev Neuroscience, vol. 33, Jan. 2010, pp. 89-108.
Shenoy et al., "Combining Decoder Design and Neural Adaptation in Brain-Machine Interfaces", Neuron, vol. 84, No. 4, Nov. 19, 2014, 16 pgs.
Shenoy et al., "Cortical Control of Arm Movements: A Dynamical Systems Perspective", Annual Rev Neuroscience, vol. 36, Jul. 8, 2013, E-Publication May 29, 2013, 26 pgs.
Simonyan et al., "New Developments in Understanding the Complexity of Human Speech Production", The Journal of Neuroscience, vol. 36, No. 45, Nov. 9, 2016, pp. 11440-11448.

(56) References Cited

OTHER PUBLICATIONS

Spuler et al., "Error-related potentials during continuous feedback: using EEG to detect errors of different type and severity", Frontiers in Human Neuroscience, vol. 9, Article 155 (2015), 10 pgs.
Stavisky et al., "A High Performing Brain-Machine Interface Driven by Low-Frequency Local Field Potentials Alone and Together with Spikes", HHS Public Access—Author Manuscript, 36 pgs., published in final form as Journal of Neural Engineering, vol. 12, No. 3, Jun. 2015.
Stavisky et al., "Decoding Speech from Intracortical Multielectrode Arrays in Dorsal "Arm/Hand Areas" of Human Motor Cortex", Annual Conference of the IEEE Engineering in Medicine and Biology Society, Jul. 2018, 5 pgs.
Suppes et al., "Brain Wave Recognition of Words", Proceedings of the National Academy of Sciences, vol. 94, No. 26, Dec. 23, 1997, 5 pgs.
Sussillo et al., "A recurrent neural network for closed-loop intracortical brain-machine interface decoders", Journal of neural engineering 9.2: 026027 Published Mar. 19, 2012, 10 pgs.
Sussillo et al., "Making brain-machine interfaces robust to future neural variability", Nature Communications, Published Dec. 13, 2016, 12 pgs.
Sutskever et al., "Generating Text with Recurrent Neural Networks", Proceedings of the 28th International Conference on Machine Learning (ICML-11). 2011, 8 pgs.
Tankus et al., "Structured Neuronal Encoding and Decoding of Human Speech Features", HHS Public Access—Author Manuscript, 11 pgs., published in final form as Nature Communications, vol. 3, 2012.
Towle et al., "ECoG Gamma Activity During a Language Task: Differentiating Expressive and Receptive Speech Areas", Brain, vol. 131, No. 8, Aug. 2008, pp. 2013-2027.
Trautmann et al., "Accurate Estimation of Neural Population Dynamics Without Spike Sorting", bioRxiv, Dec. 5, 2017, 42 pgs.
Vainio et al., "Shared Processing of Planning Articulatory Gestures and Grasping", Experimental Brain Research, vol. 232, No. 7, Jul. 2014, pp. 2359-2368.
Waldert et al., "Influence of Spiking Activity on Cortical Local Field Potentials", The Journal of Physiology, vol. 21, Nov. 1, 2013, E Publication Aug. 27, 2013, pp. 5291-5303.
Willett et al., "Improving Brain-Machine Interface Performing by Decoding Intended Future Movements", NIH Public Access—Author Manuscript, 27 pgs., published in final form as J. Neural Engineering, vol. 10, No. 2, Apr. 2013, E-Publication Feb. 21, 2013.
Wise et al., "Premotor and Parietal Cortex: Corticocortical Connectivity and Combinatorial Computations", Annu Rev Neuroscience, vol. 20, 1997, pp. 25-42.
Yang et al., "Sensorimotor Experience and Verb-Category Mapping in Human Sensory, Motor and Parietal Neurons", HHS Public Access—Author Manuscript, 29 pgs., published in final form as Cortex, vol. 92, Jul. 2017, pp. 304-319.
"Advanced Biosignal Acquisition, Processing and Analysis", g.tec medical engineering GmbH, product catalogue, 2016, 116 pgs.
"User-ready brain-computer interface applications", intendiX, g.tec product catalogue, 2016, pp. 96-97.
Ajiboye et al., "Restoration of reaching and grasping movements through brain-controlled muscle stimulation in a person with tetraplegia: a proof-of-concept demonstration", Lancet, vol. 389, No. 10081, May 6, 2017, Electronic Publication: Mar. 28, 2017, pp. 1821-1830.
Barrero et al., "Evaluation of Text Entry Methods for Interactive Digital Television Applications with Devices Alternative to Conventional Remote Controls", International Journal of Human-Computer Interaction, vol. 32, No. 10, 2016, pp. 765-776.
Bouton et al., "Restoring cortical control of functional movement in a human with quadriplegia". Nature, vol. 533, No. 7602, May 12, 2016, pp. 247-250.
Carmena et al., "Learning to Control a Brain-Machine Interface for Reaching and Grasping by Primates", PLoS Biology, vol. 1, No. 2, Nov. 2003, Electronic Publication: Oct. 13, 2003, pp. 193-208.
Cecotti et al., "One step beyond rows and columns flashes in the P300 speller: a theoretical description", International Journal of Bioelectromagnetism, vol. 13, No. 1, 2010, pp. 39-41.
Chun et al., "BCI based Hybrid Interface for 3D Object Control in Virtual Reality", IEEE International Conference on Brain-Computer Interface, Feb. 22-24, 2016, 4 pgs.
Churchland et al., "Techniques for extracting single-trial activity patterns from large-scale neural recordings.", Current opinion in neurobiology, 17(5):609-618, Oct. 2007.
Collinger et al., "Functional priorities, assistive technology, and brain-computer interfaces after spinal cord injury", Journal of Rehabilitation Research and Development, vol. 50, No. 2, 2013, pp. 145-160.
Corley et al., "Brain-Computer Interface Virtual Keyboard for Accessibility", University of Alabama: Department of Computer Science, Jun. 2012, 6pgs.
Downey et al., "Blending of brain-machine interface and vision-guided autonomous robotics improves neuroprosthetic arm performance during grasping", Journal of NeuroEngineering and Rehabilitation, vol. 13, No. 28, Mar. 18, 2016, 12 pgs.
Ethier et al., "Restoration of grasp following paralysis through brain-controlled stimulation of muscles", Nature, vol. 485, No. 7398, May 17, 2012, pp. 368-371.
Even-Chen et al., "Augmenting intracortical brain-machine interface with neurally driven error detectors", Journal of Neural Engineering, vol. 14, No. 6, Nov. 10, 2017, 16 pgs.
Fowler et al., "Improved inference and autotyping in EEG-based BCI typing systems", Proceedings of the ACM SIGACCESS Conference on Computers and Accessibility, Oct. 21-23, 2013, 8 pgs.
Ganguly et al., "Emergence of a Stable Cortical Map for Neuroprosthetic Control", PLoS Biology, vol. 7, No. 7, Jul. 21, 2009, e1000153, 13 pgs.
Hill et al., "Recording Human Electrocorticographic (ECoG) Signals for Neuroscientific Research and Real-time Functional Cortical Mapping", Journal of Visualized Experiments, 2012, vol. 64.
Hochberg et al., "Reach and grasp by people with tetraplegia using a neurally controlled robotic arm", Nature, vol. 485, No. 7398, May 17, 2012, pp. 372-375.
Hoggan et al., "Investigating the Effectiveness of Tactile Feedback for Mobile Touchscreens", Proceedings of the SIGCHI Conference on Human Factors in Computing Systems, Florence, Italy, Apr. 5-10, 2008, pp. 1573-1582.
Jarosiewicz et al., "Virtual typing by people with tetraplegia using a selfcalibrating intracortical brain-computer interface", Science Translational Medicine, vol. 7, No. 313, Nov. 11, 2015, 11 pgs.
Kao et al., "A High-Performance Neural Prosthesis Incorporating Discrete State Selection With Hidden Markov Models", IEEE Transactions on Biomedical Engineering, vol. 64, No. 4, Apr. 2017, pp. 935-945.
Kao et al., "Single-trial dynamics of motor cortex and their applications to brain-machine interfaces", Nature Communications, vol. 6, No. 7759, Jul. 29, 2015, 12 pgs.
Krusienski et al., "Control of a Visual Keyboard Using an Electrocorticographic Brain-Computer Interface", Neurorehabilitation and Neural Repair, vol. 25, No. 4, May 2011, pp. 323-331, doi:10.1177/1545968310382425.
Lau et al., "A Special Virtual Keyboard for Disabled Computer Users", Proceedings of the International MultiConference of Engineers and Computer Scientists, Mar. 15-17, 2017, 6 pgs.
Llera, "Adaptive Classification on Brain-Computer Interfaces Using Reinforcement Signals", Neural Computation, 2012.
Lopez et al., "Text entry with the Apple iPhone and the Nintendo Wii", Proceedings of the Twenty-Seventh Annual SIGCHI Conference on Human Factors in Computing Systems, Boston, USA, Apr. 4-9, 2008.
Mackenzie et al., "Text Entry for Mobile Computing: Models and Methods, Theory and Practice", Human-Computer Interaction, vol. 17, No. 2-3: Text Entry for Mobile Computing, Sep. 2002, pp. 147-198.
Makin, "Brain-Computer Interface Allows Speediest Typing to Date", Scientific American, Feb. 21, 2017, 5 pgs.

(56) References Cited

OTHER PUBLICATIONS

Mayaud et al., "Robust Brain-computer interface for virtual Keyboard (RoBIK): project results", IRBM, Elsevier Masson, vol. 34, No. 2, 2013, pp. 131-138.
Moritz et al., "Direct control of paralysed muscles by cortical neurons", Nature, vol. 456, No. 7222, Dec. 4, 2008, pp. 639-642.
Musallam et al., "Cognitive Control Signals for Neural Prosthetics", Science, vol. 305, No. 5681, Jul. 9, 2004, pp. 258-262.
Noorzadeh et al., "Beyond 2D for brain-computer interfaces: two 3D extensions of the P300-speller", Proceedings of the IEEE International Conference on Acoustics, Speech, and Signal Processing, May 2014, pp. 5940-5944.
Nuyujukian et al., "A High-Performance Keyboard Neural Prosthesis Enabled by Task Optimization", IEEE Transactions on Biomedical Engineering, vol. 62, No. 1, Jan. 2015, pp. 21-29.
Nuyujukian et al., "A Nonhuman Primate Brain-Computer Typing Interface", Proceedings of the IEEE, vol. 105, No. 1, Jan. 2017, pp. 66-72.
Orhan et al., "RSVP Keyboard: An EEG Based Typing Interface", Proceedings of the IEEE International Conference of Acoustics Speech and Signal Processing, Sep. 12, 2013, 11pgs.
Paninski et al., "Neural data science: accelerating the experiment-analysis-theory cycle in large-scale neuroscience", Current Opinion in Neurobiology, vol. 50, Jun. 2018, pp. 232-241.
Serruya et al., "Brain-machine interface: Instant neural control of a movement signal", Nature, vol. 416, No. 6877, Mar. 14, 2002, pp. 141-142.
Smith et al., "Optimizing Touchscreen Keyboards for Gesture Typing", Proceedings of the 33rd Annual ACM Conference on Human Factors in Computing Systems, Seoul, Korea, Apr. 18-23, 2015, pp. 3365-3374.
Subasi et al., "EEG signal classification using PCA, ICA, LDA and support vector machines", Expert Systems with Applications, 2 010, vol. 37, pp. 8659-8666.
Taylor et al., "Direct Cortical Control of 3D Neuroprosthetic Devices", Science, vol. 296, No. 5574, Jun. 7, 2002, pp. 1829-1832.
Velliste et al., "Cortical control of a prosthetic arm for self-feeding", Nature, vol. 453, No. 7198, Jun. 19, 2008, pp. 1098-1101.
Venkatagiri, "Clinical measurement of rate of reading and discourse in young adults", Journal of Fluency Disorders, vol. 24, No. 3, Sep. 1999, pp. 209-226.
Wang et al., "P300 Brain-Computer Interface Design for Communication and Control Applications", Proceedings of the IEEE International Conference of Engineering in Medicine and Biology, Sep. 1-4, 2005, 4pgs.
Zhang et al., "Converting Your Thoughts to Texts: Enabling Brain Typing via Deep Feature Learning of EEG Signals", arXiv: 1709.08820, Sep. 26, 2017, 10 pgs.
International Search Report and Written Opinion for International Application No. PCT/US2021/040192, Search completed Nov. 6, 2021, dated Dec. 9, 2021, 21 Pgs.
Bocquelet, "Toward a Brain-Computer Interface for Speech Restoration", Electronics. Universite Grenoble Alpes, 2017. English. ffNNT: 2017GREAS008ff. fftel-01693270f.
Branco et al., "Decoding Hand Gestured from Primary Somatosensory Cortex Using High-Density ECoG", Neuroimage, Feb. 15, 2017, vol. 147, pp. 130-142.
Brumberg et al., "Brain-Computer Interfaces for Speech Communication", Speech Communication, Apr. 1, 2010, vol. 52, Issue 4, pp. 367-369.
Chen et al., "High-Speed Spelling with a Noninvasive Brain-Computer Interface", Proceedings of the National Acad Sci, 112, 2015, pp. E6058-E6067.
Christie et al., "Comparison of Spike Soring and Thresholding of Voltage Waveforms for Intracortical Brain-Machine Interface Performance", Journal of Neural Engineering, 12, 2014, 016009.
Jarosiewicz et al., "Virtual typing by people with tetraplegia using a self-calibrating intracortical brain-computer interface", Science Translational Medicine, 7, 2015.
Makin et al., "Machine Translation of Cortical Activity to Text with an Encoder-Decoder Framework", Nature Neuroscience 1-8, 2020, DOI 10.1038/s41593-020-0608-8.
Willett et al., "Hand Knob Area of Premotor Cortex Represents the Whole Body in a Compositional Way", Cell, 2020, DOI: 10.1016/j.cell.2020.02.043.
Yousry et al., "Localization of the motor hand area to a knob on the precentral gyrus. A new landmark", Brain, 120, 1997, pp. 141-157.

\* cited by examiner

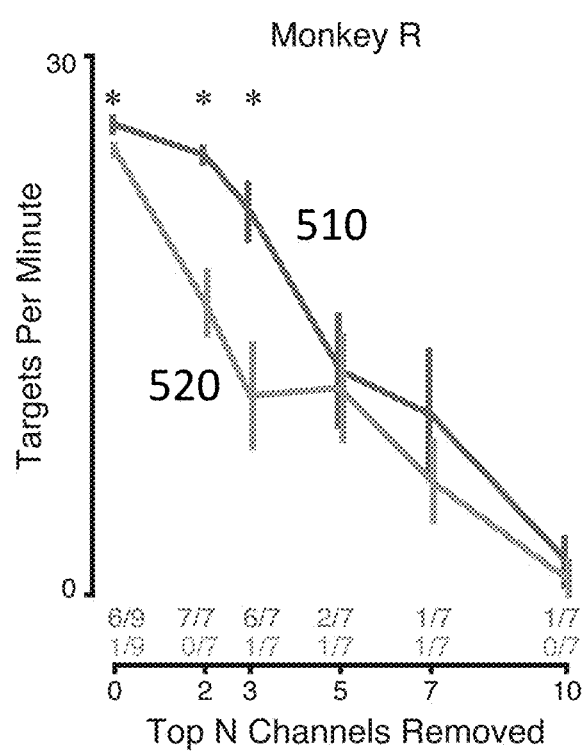 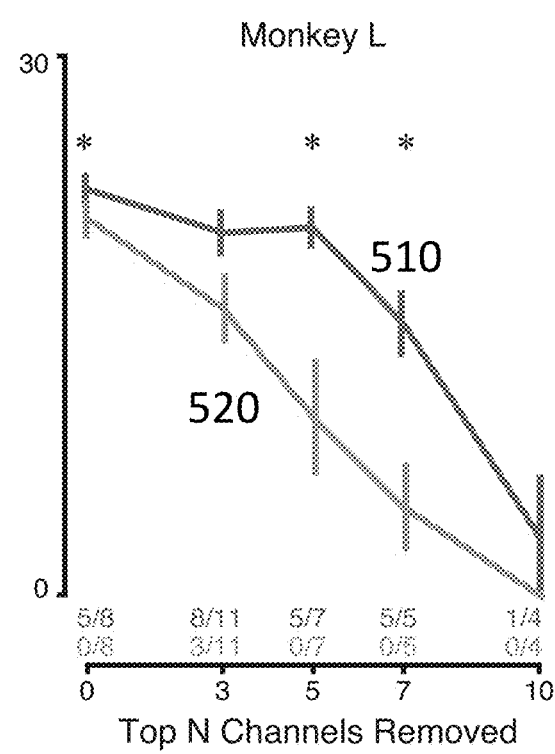
FIG. 5A  FIG. 5B

MULTIPLICATIVE RECURRENT NEURAL NETWORK FOR FAST AND ROBUST INTRACORTICAL BRAIN MACHINE INTERFACE DECODERS

CROSS-REFERENCE TO RELATED APPLICATIONS

This application is a continuation of U.S. patent application Ser. No. 14/826,300 filed Aug. 14, 2015, U.S. Pat. No. 10,223,634 issued Mar. 5, 2019, which is incorporated herein by reference.

U.S. patent application Ser. No. 14/826,300 filed Aug. 14, 2015 claims priority from U.S. Provisional Patent Application 62/037,441 filed Aug. 14, 2014, which is incorporated herein by reference.

STATEMENT OF GOVERNMENT SPONSORED SUPPORT

This invention was made with Government support under contracts 8DP1HD075623-04, R01NS076460 awarded by the National Institutes of Health, and under contract N66001-10-C-2010 awarded by the Defense Advanced Research Projects Agency. The Government has certain rights in the invention.

FIELD OF THE INVENTION

This invention relates to decoders for brain machine interfaces.

BACKGROUND OF THE INVENTION

Brain-machine interface (BMI) systems convert neural signals from motor regions of the brain into control signals to guide prosthetic devices. The ultimate goal of BMIs is to improve the quality of life for people with paralysis by providing direct neural control of prosthetic arms or computer cursors. While considerable research over the past 15 years has led to compelling BMI demonstrations, there remain several challenges to achieving clinically viable BMI systems. In this invention, we focus on the challenge of increasing BMI performance and robustness.

SUMMARY OF THE INVENTION

The present invention provides a brain machine interface (BMI) to control a device. The BMI has a neural decoder, which is a neural to kinematic mapping function with neural signals as the input to the neural decoder and kinematics to control the device as the output of the neural decoder. The neural decoder is based on a continuous-time multiplicative recurrent neural network, which has been trained as a neural to kinematic mapping function. The device to be controlled could be a robotic arm, a prosthetic device or a cursor on a computer screen.

In one embodiment, the outputted kinematics could be normalized position over time and velocity over time.

In another embodiment, the neural training data used for training of the neural to kinematic mapping function has been modified. The neural training data could, for example, be modified by randomly adding and removing spikes such that the mean number of spikes is preserved on average.

In yet another embodiment, the neural decoder could have been trained with neural and kinematic data sets collected over multiple days.

In yet another embodiment, the neural decoder could have been trained with neural and kinematic data sets collected over five or more days.

Embodiments of the invention offer the following advantages:

1. State of the art robustness to variations and perturbations in the day-to-day and moment-to-moment neural data. This robustness may help to enable the clinical use of BMIs.
2. State of the art performance of the neural decoder.
3. The ability to improve the decoder by using data from previous days, something the previous decoders were unable to do.

BRIEF DESCRIPTION OF THE DRAWINGS

FIG. 2B shows an MRNN (210) and FIT-long (blue) decoder were trained using data from all of the recording sessions in FIG. 2A. The plots show the decoding accuracy of each decoder when decoding hand velocity from held-out trials from each of these days. Note that the horizontal axis now shows chronological days instead of consecutive recording session number as in FIG. 2A.

FIGS. 5A-B shows that the MRNN is robust to unexpected loss of neural input channels. Closed-loop BMI performance using the MRNN (510) and FIT-KF (520) decoders while simulating an unexpected loss of 0 to 10 channels by setting the firing rates of these channels to zero. The grand mean and SEM of performance is shown for each decoder as a function of how many channels were removed. Stars denote conditions for which the MRNN significantly outperformed FIT-KF across sessions (p<0.05, paired t-test). The fractions above each condition specify for how many of the individual evaluation days each decoder performed significantly better according to success rate and time to target. Channel-dropping order was determined by the mutual information between that channel's spike count and target direction during arm-controlled reaches. Top line tick mark numbers above the x-axis are for 510, while the bottom line tick mark number above the x-axis are for 520.

FIG. 6A shows robustness to channel dropping. We evaluated the closed-loop BMI performance of the MRNN decoder trained with (610) and without (620) the training data spike rate perturbation innovation. Both decoders were evaluated on the same days with firing rates on the top 0 to 10 channels set to zero (similar to FIGS. 4A-B). Each circle corresponds to a decoder's mean performance on a given evaluation day. Filled circles denote days where there was a significance performance difference (p<0.05) between the two decoders tested. The line shows the grand mean performance for each decoder. The MRNN trained with perturbed firing rates consistently outperformed the MRNN trained without these training data perturbations when faced with channel-dropped neural input. FIG. 6B shows historical training data experiments. MRNNs were trained without access to recent training data, as in FIG. 3A-C, either with (630) or without (640) training data spike rate perturbations. We trained decoders from both of monkey R's historical training data periods and from monkey L's longer historical training data period. Closed-loop BMI performance using these decoders was then compared on the same evaluation day in alternating blocks. The plot shows the mean time to target for each block. For all three pairs of decoders compared, the MRNN with spike rate perturbations had significantly faster times to target (p<0.05 averaged across all trials). Datasets R.2014.03.21 & L.2014.04.04.

DETAILED DESCRIPTION OF THE INVENTION

Figure 1:
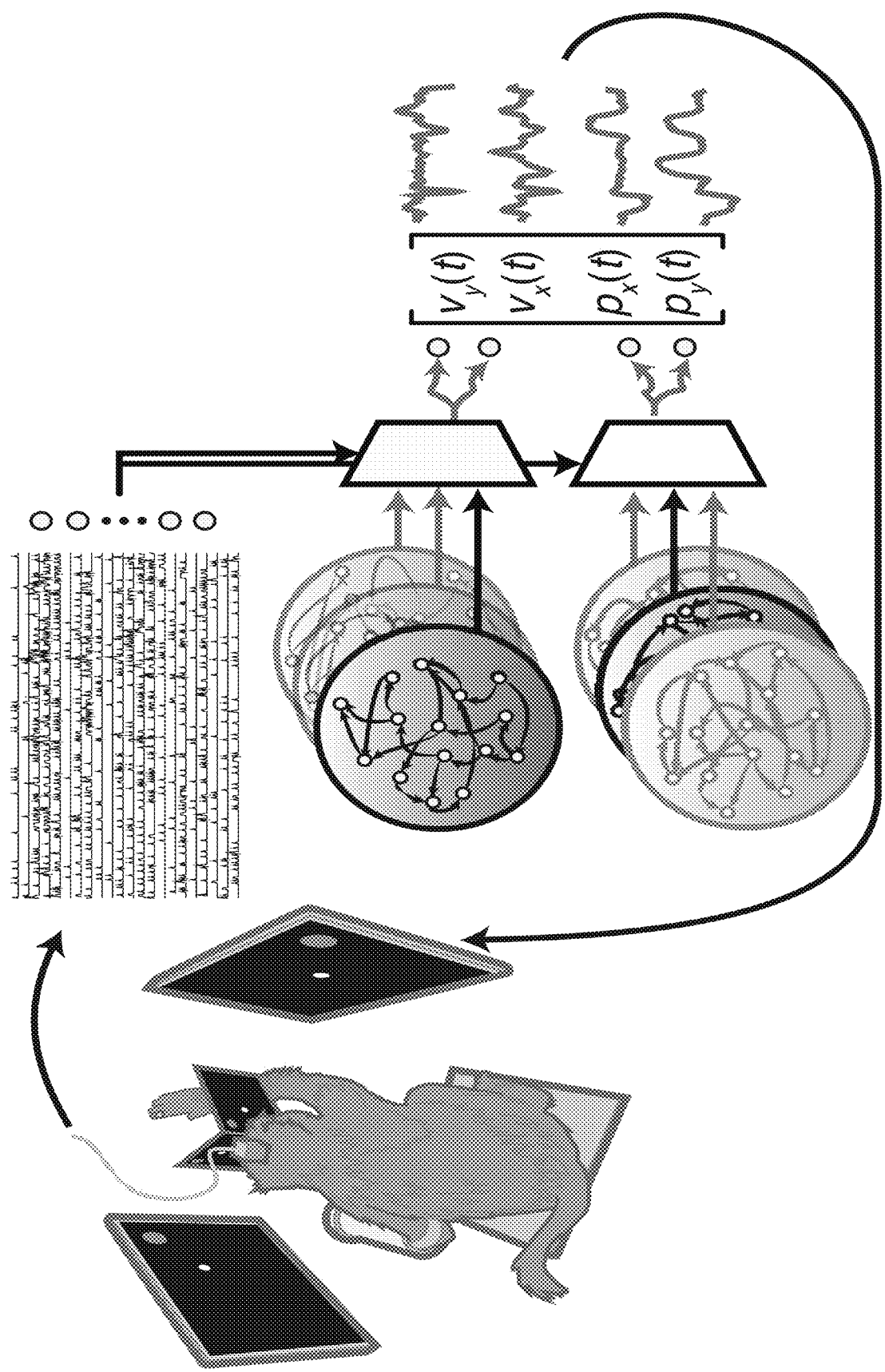
FIG. 1 shows a schematic of the experimental setup and MRNN (Multiplicative Recurrent Neural Network) decoder. A monkey performed a target acquisition task using his hand while multiunit spikes were recorded from two multi-electrode arrays in motor cortex. Data from many days (e.g. 2 or more days, preferably 5 or more days) of this task were used to train two parallel MRNNs such that velocity and position could be read out from the state of their respective internal dynamics. These internal dynamics are a function of the binned spike counts; thus, the MRNN architecture can conceptually be thought of as selecting which internal dynamics rules are active at any given time based on the spike count inputs. During closed-loop use, the decoded velocity and position commands from the parallel networks were blended together to continuously update the cursor position displayed back to the monkey.
Figure 2A:
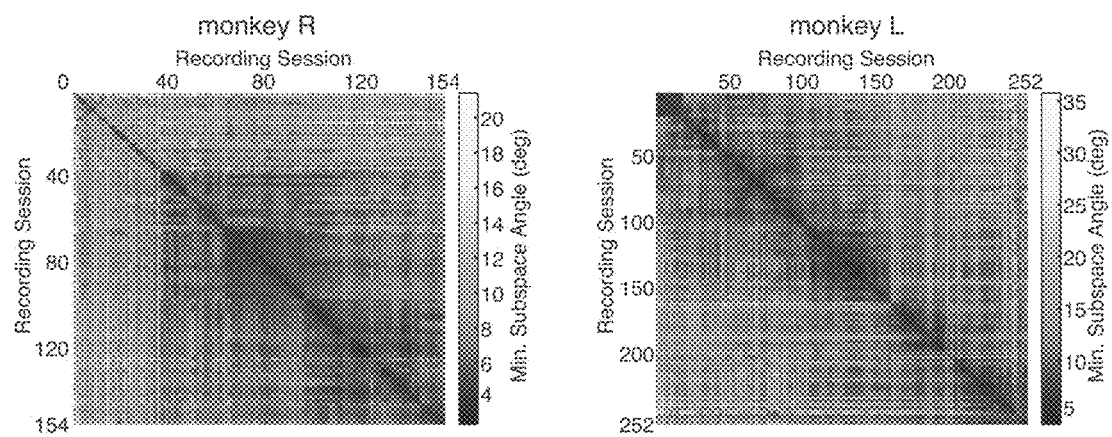
FIGS. 2A-B FIG. 2A shows between-day variability of the structure of neural activity recorded during center-out reaching over the course of many months. The shading at the intersection of row i and column j, corresponds to how differently the observed neural activity covaried during recording sessions i and j. Specifically, we have plotted the minimum subspace angle between subspaces spanned by the top 10 eigenvectors of each day's mean-activity-subtracted covariance matrix. These 10 eigenvectors captured on average 51 (46)% of single-trial variance for monkeys R (L).
Figure 2B:
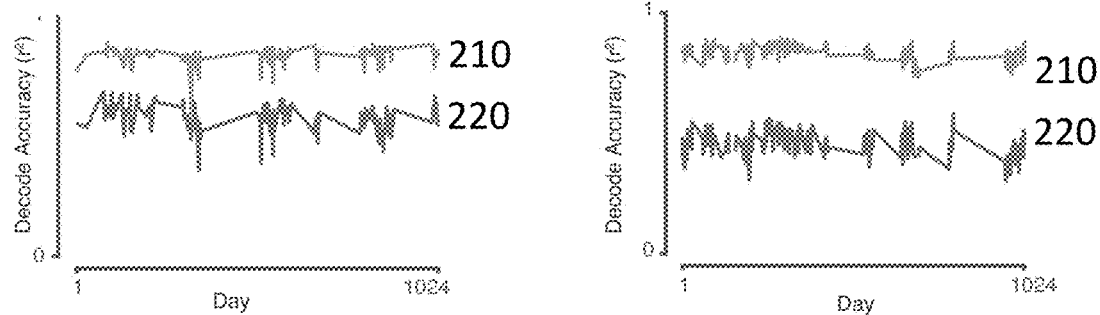
Figures 3A, 3B, 3C:
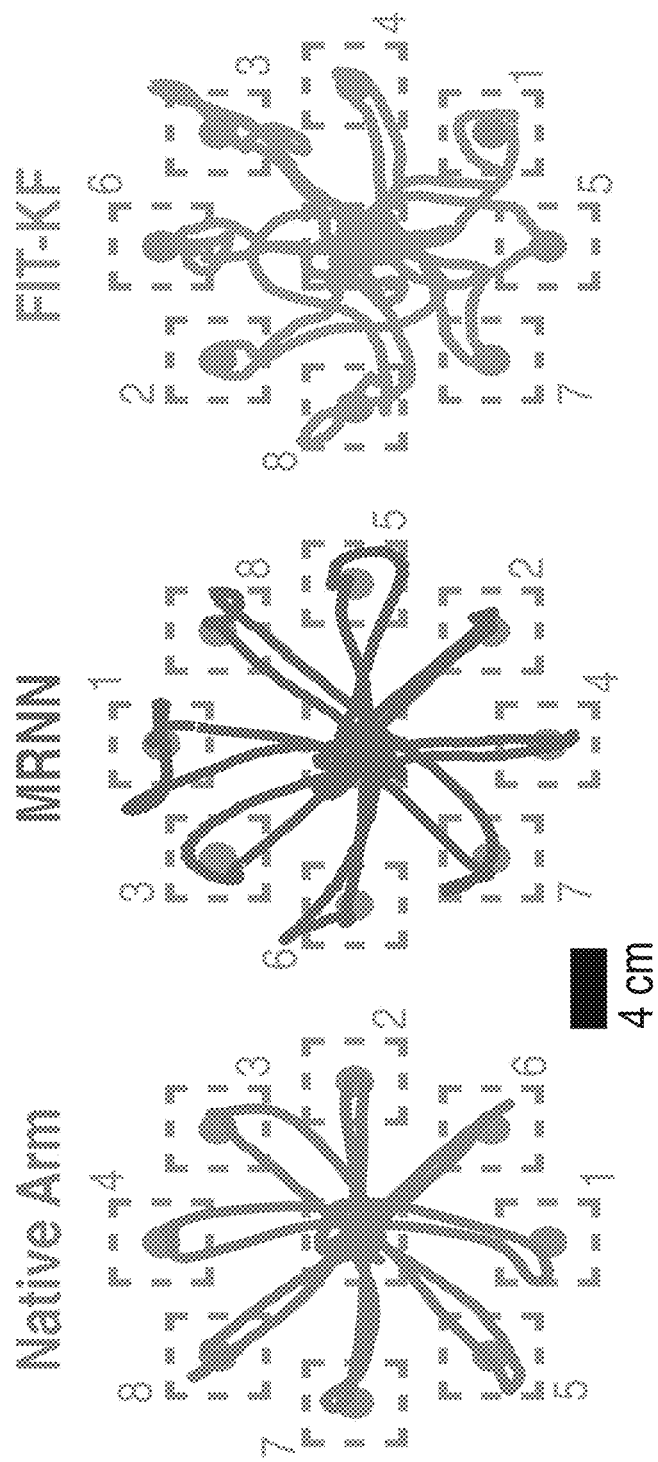
FIGS. 3A-C show an example of high performance closed-loop BMI control using the MRNN Decoder. Cursor trajectories from eight representative and consecutive center-out-and-back trials of a Radial 8 Task in which the subject had to move a cursor over a target which alternated between the center of the workspace and one of the peripheral locations. The cursor was either controlled by the monkey's hand position (FIG. 3A), the MRNN decoder (FIG. 3B), or the FIT-KF decoder trained from the same day's training data (FIG. 3C). The FIT-KF decoder is the existing state of the art for BMI decoding algorithms. The bounding boxes show the target acquisition area, and the order of target presentation is denoted with green numbers. Dataset R.2014.04.03.
Figures 4A, 4B:
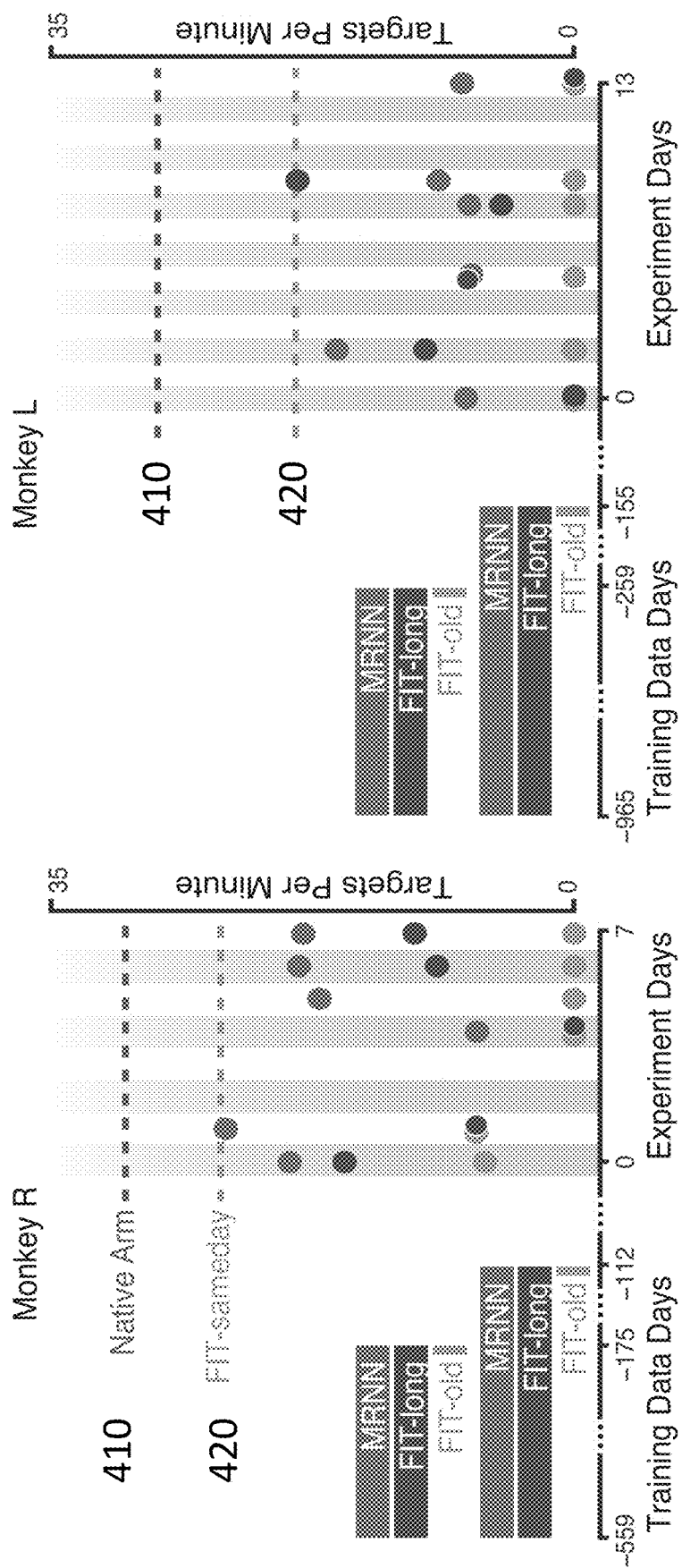
FIGS. 4A-B show for two monkeys that the MRNN is robust to a natural sampling of neural variability despite trained without access to the most recent several months of data. Each circle corresponds to the mean closed-loop BMI performance using MRNN (medium grey), FIT-long (dark grey), and FIT-old (light grey) decoders when evaluated on six different experiment days. The labeled rectangles denote the time periods from which training data for each decoder came from. The triplet of decoders with the more recent available training day was evaluated on the first three experiment days, and the triplet with less (and more distant) training data was evaluated on the last three experiment days. For both monkeys, only the MRNN decoder consistently was able to perform the task. To aid the interpretation of these historical decoder performances, the dotted lines show the average performance across the experiment days using the native arm (410) or a FIT decoder trained from that same day's arm reaches (420).
Figure 6A:
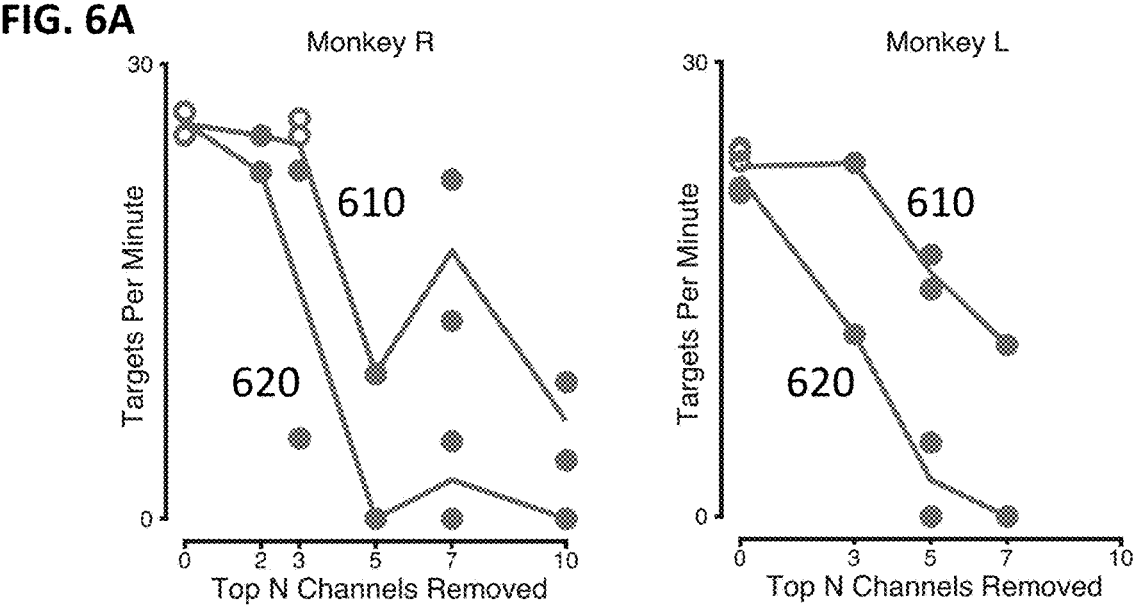
FIGS. 6A-B show that training data spike rate perturbations improve closed-loop MRNN performance.
Figure 6B:
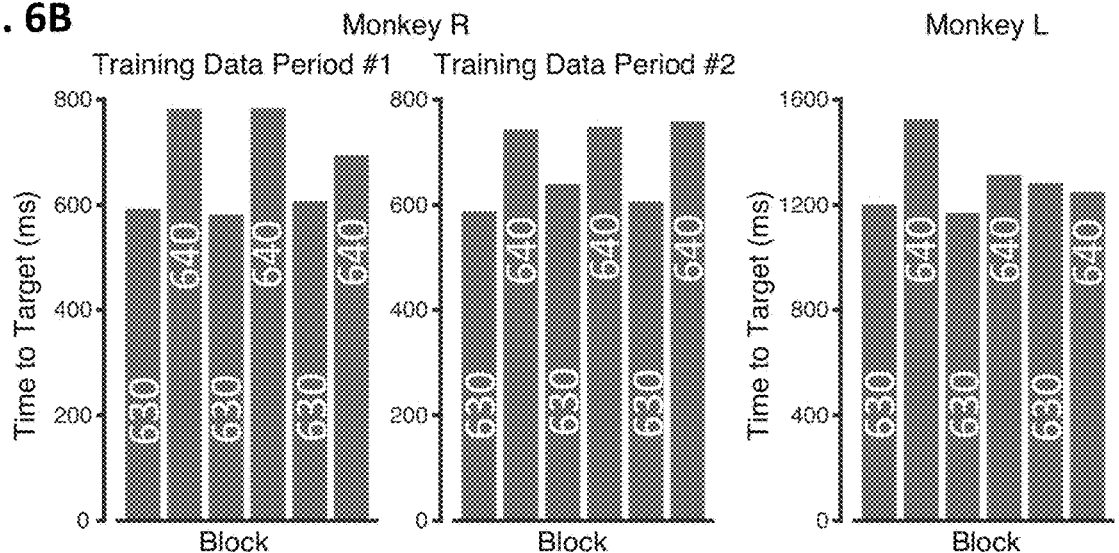

The present invention also referred to as Big-Data Multiplicative Recurrent Neural Network (BD-MRNN) is a supervised neural network and training method for incorporating and modifying multiple previous days training datasets (historical data) to improve both raw performance and robustness in the daily operation of brain-machine interface (BMI) decoders.

MRNN Definition

The generic recurrent network model is defined by an N-dimensional vector of activation variables, x, and a vector of corresponding "firing rates", r=tan h(x). Both x and r are continuous in time and take continuous values. In a standard RNN model, the input affects the dynamics as an additive time-dependent bias in each dimension. In the MRNN model, the input instead directly parameterizes the weight matrix, allowing for multiplicative interactions between the input and the hidden state. One view of this multiplicative interation is that the hidden state of the recurrent network is selecting an appropriate decoder for the statistics of the current dataset. The equation governing the dynamics of the activation vector is of the form suggested in Suskever 2011, but adapted for this invention to continuous time $$\tau \dot{x}(t) = -x(t) + J^{u(t)} r(t) + b^x. \tag{0.1}$$

The N×N×F tensor $J^{u(t)}$ defines the values of the recurrent connections of the network, which are dependent on the I-dimensional input, u(t). In the MRNN, $J^{u(t)}$ is factorized such that the input is linearly combined into F factors. Specifically, $J^{u(t)}$ is factorized according to $$J^{u(t)} = J^{xf} \cdot \mathrm{diag}(J^{fu} u(t)) \cdot J^{fx}, \tag{0.2}$$

where $J^{xf}$ has dimension N×F, $J^{fu}$ has dimension F×I, $J^{fx}$ has dimension F×N, and diag(v) takes a vector, v, and returns a diagonal matrix with v along the diagonal. One directly controls the complexity of interactions by choosing the number of factors, F. If $F=N^2$, we recover a full N×N×N tensor. If F=1, $J^{u(t)}$ is a a rank-one matrix whose singular value is function of u(t).

Finally, the network has a constant bias, $b^x$, and the neuronal time constant, $\tau$, sets the time scale of the network.

MRNN Output Definition

The output of the network is a weighted sum of the network firing rates plus a bias, defined by $$z(t) = W_O^T r(t) + b^z, \tag{0.3}$$

where $W_O$ is an N×M matrix and $b^z$ is an M-dimensional bias.

Network Construction for Cursor BMI Decoder

The network equations defined above are used according to the following procedures and parameters in order to build the BD-MRNN BMI decoder.

MRNN Initialization

For our online experiments, the size of the networks are set to N=100 and N=50 with F=N in both cases (see Table 1). One subject uses a single multi-unit electrode arrays (I=96), while the second uses two (I=192). The non-zero elements of the non-sparse matrices $J^{xf}$, $J^{fu}$, $J^{fx}$ are drawn independently from a Gaussian distribution with zero mean and variance $g_{xf}/F, g_{fu}/I$, and $g_{fx}/N$ with $g_{xf}$, $g_{fu}$, and $g_{fx}$ defined in Table 1 for the specific BMI task. The elements of $W_O$ are initialized to zero, and the bias vectors $b^x$ and $b^z$ are also initialized to 0.

Concatenating Neural Trials for Seeding the MRNN during Training

The input u(t), to the MRNN, is the vector of binned spikes measured from neural data (see, for example, Sussillo 2012 for details on standard preprocessing of neural signals, see Δt in Table 1 for bin sizes). By input to the MRNN, we mean in the sense of equation 0.1. This results in a data matrix, $U^j$, of binned spikes of size I×$T^j$ for each actual trial, where $T^j$ is the number of time steps for the $j^{th}$ trial. Five actual trials are then concatenated together to make one "training" trial. The first two actual trials in a training trial are used for seeding the hidden state of the MRNN, and are not used for learning, whereas the final 3 actual trials in the training trial are used for learning. In this way, excepting the first two actual trials in the day's dataset, the entire set of actual trials are used for learning, by incrementing the actual trial index that begins a training trial.

Perturbing the Neural Input during Training

A key element of training robustness to nonstationarities in the neural code is the introduction of perturbations to the neural spike trains that are used to train the MRNN. The concatenated input in a given training trial, $\hat{U}=[U^i, \ldots, U^{i+4}]$ are perturbed by adding and removing spikes from each channel. We focus on channel c of the $j^{th}$ training trial, i.e., a row vector of data, $\hat{U}_{c,:}^j$. Let the number of spikes in $\hat{U}_{c,:}^j$ be $n_c^j$ before perturbation. This number is perturbed according to $$\hat{n}_c^j = \eta^j \eta_c n_c^j, \qquad (0.4)$$

where both $\eta^j$ and $\eta_c$ are Gaussian variables with a mean of one and standard deviations of $\sigma_{trial}$ and $\sigma_{channel}$, respectively (see Table 1). Conceptually, $\eta^j$ models a global modulation in the array across all channels (e.g. changes in subject arousal), while $\eta_c$ models channel by channel perturbations, such as uncontrolled channel dropping or moving baselines in individual neurons. If $\hat{n}_c^j$ is less than zero or greater than $2n_c^j$, it is resampled according to equation 0.4, which keeps the average number of perturbed spikes in a given channel and training trial the same as the average number of unperturbed spikes in the same channel and training trial. Otherwise, if $\hat{n}_c^j$ greater than $n_c^j$, then $\hat{n}_c^j - n_c^j$ spikes are added to random time bins of the the training trial. If $\hat{n}_c^j$ is less than $n_c^j$, then $n_c^j - \hat{n}_c^j$ spikes are randomly removed from time bins of the training trial that already had spikes. Finally, if $\hat{n}_c^j = n_c^j$, nothing is changed.

The process of perturbing the binned spiking data occurs on every iteration of the optimization algorithm. For example, in a batch gradient descent algorithm, the perturbation described by equation 0.4 happens after each update of the network parameters.

Using Many Days Training data

The typical methodology for training a closed-loop BMI decoder involves training on a session-by-session basis. This means that every day, the subject engages in a control task, for which both input (neural) and supervisory (kinematics) signals are collected. After this session-by-session training period, a BMI is optimized to perform well on this data exclusively.

The second critical component to achieving both performance and robustness in the BD-MRNN decoder is using many days of training data. In our laboratory experiments, we use multiple years of training data (see Table 1). Because of the extreme nonstationarities of the neural data, this aspect of the BD-MRNN training methodology is unintuitive. The nonlinear, multiplicative architecture of the MRNN utilizes the regularities that across many days do exist in a dataset comprising many days. In comparison, the (due to BD-MRNN, no longer) state-of-the-art linear Kalman Filter methods, including previous days data would result in potentially very poor decoders.

Network Output

We train two MRNN networks to each output a 2-dimensional signal. One network is trained to output the normalized position through time in both the horizontal (x) and vertical (y) spatial dimensions. The other MRNN is trained to output the velocity through time, also in the x and y dimensions. We calculate the hand velocities from the positions numerically using central differences.

Since the MRNN decoder outputs both normalized position and velocity, we combine both for our final decoded position signal. The decode used during BMI mode, $d_x(t)$, $d_y(t)$ is a mix of both velocity and position, defined by $$d_x(t) = \beta(d_x(t-\Delta t) + \gamma_v v_x(t-\Delta t)\Delta t) + (1-\beta)\gamma_p p_x(t) \qquad (0.5)$$

$$d_y(t) = \beta(d_y(t-\Delta t) + \gamma_v v_y(t-\Delta t)\Delta t) + (1-\beta)\gamma_p p_y(t), \qquad (0.6)$$

where $v_x$, $v_y$, $p_x$, $p_y$ are the normalized velocity and positions in the x and y dimensions and $\gamma_v$, $\gamma_p$ are factors that convert from the normalized velocity and position, respectively, to the physical values associated with the workspace. The parameter $\beta$ sets the amount of velocity vs. position decoding (see Table 1).

Training and Running the Networks

A network is simulated by integrating equation 0.1 using the Euler method at a time step of $\Delta t = \tau/5$ and then evaluating equation 0.3.

The parameters of the network are trained offline to reduce the averaged squared error between the measured kinematic training data and the output of the network, $z(t)$. Specifically, we use the Hessian-Free (HF) optimization method for RNNs (but adapted to the continuous-time MRNN architecture). HF is an exact $2^{nd}$ order method that uses back-propagation-through-time to compute the gradient of the error with respect to the network parameters. The set of trained parameters is $\{J^{xf}, J^{fu}, J^{fx}, b^x, b^z\}$. The HF algorithm has some critical parameters, such as the mini-batch size, the initial lambda setting, and the max number of CG iterations. We set these parameters to $\frac{1}{5}$ times the total number of trials, 0.1, and 50, respectively.

After training, the networks are copied into the embedded real-time environment (xPC), and run in closed-loop, to operate online in BMI mode. Specifically, at each time point the RNN module receives binned spikes and outputs the current estimate of the hand position, which is used to display the cursor position on the screen. During BMI mode the neural spikes are not perturbed in any way. The values $v_x(0)$ and $v_y(0)$ are initialized to 0, as is the MRNN hidden state.

Model Parameters

The parameters of the model of an exemplary embodiment are listed in Table 1.

TABLE 1

Values for network and training parameters for Monkeys R and L, as described in the invention report.

|  | Monkey R | Monkey L |
|---|---|---|
| $\Delta t$ | 20 ms | 30 ms |
| $\tau$ | 100 ms | 150 ms |
| N | 100 | 50 |
| F | 100 | 50 |
| $\sigma_{trial}$ | 0.045 | 0.045 |
| $\sigma_{channel}$ | 0.3 | 0.3 |
| $g_{xf}$ | 1.0 | 1.0 |
| $g_{fu}$ | 1.0 | 1.0 |
| $g_{fx}$ | 1.0 | 1.0 |
| I | 192 | 96 |
| # years training data | 0.25 to 3 | 0.25 to 3 |
| $\beta$ | 0.99 | 0.99 |

Remark on the Use of Multiple Days of Training Data

One critical aspect of the invention is using multiple days of training data. At first glance, it may seem straightforward that more data should always improve the quality of performance on some supervised system, such as a neural network. However, this is only true under a very specific and very commonly met assumption. This assumption is *not* met in the BMI setting. The assumption is that the data used to optimize ("train") the neural network comes from the same distribution as the data used in the network during operation (during so-called "validation" or "testing"). When this assumption is met, indeed more training data leads to a better neural network that performs better on generalization testing. To reiterate, this assumption is *not* met in the neural data used to train BMIs.

As an example analogous to the BMI setting, imagine that we are interested in building a neural network to classify hand written letters from different users. Specifically, we want to classify different users based on how they write the letter 'h' (e.g. user 1 wrote these 'h' letters, while user 2 wrote those 'h' letters.) If our dataset contained only handwritten 'h' letters, then adding more and more 'h' letters would definitely improve our classification of user 1 from user 2, as per common understanding. However, imagine that we had access to other letters that the users wrote, such as 'n', and 'x'. If our job is only to classify different users based on the letter 'h', then it appears that including 'x' as training data to an 'h' classifier could only hurt the it's performance on classifying the letter 'h'.

However, you could also reason that if you included 'n' in your 'h' classifier, perhaps one could still improve the classifier because the letter 'n' shares some common features with the letter 'h'. It's not at all clear what would happen if we threw in the letters from 'a' to 'z'. We can summarize that adding more training data (letters different from 'h'), when the data does not come from the test distribution ('h' letters), will not obviously help improve the network's performance.

The previous example is analogous to current situation in BMI research. We would like to classify different user intentions, such as moving a computer cursor up or down (analogous to classifying user 1 or user 2) based on neural data (the letters). However, each day the neural data upon which we classify changes dramatically (some days we have 'h' letters to classify user 1 vs user 2, some days we have 'x' letters). Further, the changes in neural data are not under our control. So we never know whether we are going to be looking at an 'h' or an 'x' or a 'n'. If it's an 'h' day, than using a previous 'x' day seems like a bad idea.

It is a fact, in the BMI setting, the neural data collected using modern devices (e.g., Utah multi electrode array) varies dramatically from day-to-day, even when the subject is requested to perform the exact same task, and the experimental conditions are reproduced to as exacting conditions as the experimental environment will allow. It is unclear why the neural data varies so dramatically, although many believe it is a combination of the underlying complexities of the neural code, combined with the inevitable limitations of reading biological electrical signals with limited silicon-based hardware.

The variation in neural signals has led to the widely held view in the BMI field that using data from multiple days is in fact quite problematic. As a result, the standard—and state of the art—practice is to record training data each and every day, and perhaps more than once a day. This training data is then used to run a BMI decoder for some amount of time on that same day. Anecdotally, many researchers have tried to incorporate more data than just a single day, though it is widely held as a bad idea because it often fails to improve things. Sometimes using yesterday's data as well as today's data improves things, sometimes it does not. Surely using data from over 1 month ago is a bad idea to include in a training set for today's BMI decoder.

These widely held views about which data to use for training a closed-loop BMI decoder are based primarily on using a linear decoding method, the Kalman filter. As a linear method, the Kalman filter can only give an average response to many days of training data, so if neural data from one month ago is indeed different from today's neural data, indeed the Kalman filter trained using the old data will result in a very poor decoder on new data from today. Thus the vast majority of experts (likely all) in the field would consider it non-straightfoward to devise a method whereby previous data from three to six months ago, as we have shown empirically, is helping to decode today's neural data.

For our invention, we made a systematic study of how one day's neural data compares to another day's. We did this using an analysis technique called the principal subspace angle. The scientific result of this analysis is that some days are more similar to others, while some days are very different. Further, similar neural data tends to come in blocks of time, but oddly, data from many months ago can be quite similar to today's neural data (the exact similarity structure is beyond the scope of this introduction). Naturally, it would be desirable to use only training data from days that are similar to the day on which you were interested in running the decoder (use 'n's and not 'x's to help classify the users 1 and 2 based on how they write the letter 'h'). However, it is very hard to know, a priori, which days will help.

To sidestep this problem, we used a highly nonlinear decoder, a multiplicative recurrent neural network (MRNN). The MRNN is powerful enough to handle the varying neural data from many days, even when the neural data is significantly different from day to day. So long as there are some similarities in the neural data between days (e.g. a 'n' similar to an 'h'), the MRNN is smart enough to use this data to improve the BMI decode. If the training data bears little similarity to today's neural data ('x' letters are not similar to 'h' letters), the MRNN is smart enough to ignore it while decoding today's neural data.

Embodiments of the invention could be envisioned as a brain machine interface controlling a device such as a robotic arm, a prosthetic device or a cursor on a computer screen. The brain machine interface receives neural signals from a subject's brain, which are processed by one or more neural decoders. The neural decoders are either functionalized with method steps to execute the signal processing steps and/or are hardware systems for processing the neural signals as described herein. The neural decoders could include computer hardware and software devices/technology for its operation(s). The neural decoders are interfaced with the device to control the kinematics of the device based on the processed neural signals.

REFERENCES

John P Cunningham et al. A closed-loop human simulator for investigating the role of feedback control in brain-machine interfaces. Journal of neurophysiology, 105 (4):1932-1949, April 2011.
Cynthia A Chestek et al. Long-term stability of neural prosthetic control signals from silicon cortical arrays in rhesus macaque motor cortex. Journal of neural engineering, 8(4):045005, July 2011.
Gopal Santhanam et al. A high-performance brain-computer interface. Nature, 442(7099):195-198, July 2006.
S I Ryu. Human cortical prostheses: lost in translation? Neurosurgical Focus, 2009.

Mark M Churchland et al. Techniques for extracting single-trial activity patterns from large-scale neural recordings. Current opinion in neurobiology, 17(5): 609-618, October 2007.

Kim et al. Neural control of computer cursor velocity by decoding motor cortical spiking activity in humans with tetraplegia. Journal of neural engineering, 5(4): 455-476, December 2008.

Sutskever, Ilya et al. Generating text with recurrent neural networks. Proceedings of the 28th International Conference on Machine Learning (ICML-11). 2011.

Sussillo, David, et al. A recurrent neural network for closed-loop intracortical brain-machine interface decoders. Journal of neural engineering 9.2 (2012): 026027.

What is claimed is:

1. A brain-machine interface system, comprising:
at least one multi-electrode array implanted into a user's brain;
a prosthetic device; and
a neural signal decoder implemented using a computing device in communication with the at least one multi-electrode array and the prosthetic device, where the neural signal decoder comprises a recurrent neural network trained by:
obtaining a plurality of neural signals from a user using the at least one multi-electrode array, where:
the plurality of neural signals are obtained over the course of at least two days; and
the plurality of neural signals is modified by randomly adding and removing neural spikes such that the mean number of neural spikes is preserved;
instantiating the recurrent neural network, where the recurrent neural network is configured to map neural signals to kinematic functions of the prosthetic device; and;
training the recurrent neural network using the plurality of neural signals; and
where the neural signal decoder is configured to:
obtain a neural signal from the user using the at least one multi-electrode array describing an intended movement of the prosthetic device using the at least one multi-electrode array;
move the prosthetic device using the trained recurrent neural network to match the intended movement of the user.

2. The brain-machine interface system of claim 1, wherein the prosthetic device is a robotic arm.

3. The brain-machine interface system of claim 1, wherein the prosthetic device is a virtual cursor.

4. The brain-machine interface system of claim 1, wherein the at least one multi-electrode array is implanted into the motor cortex of the user.

5. The brain-machine interface system of claim 1, wherein the recurrent neural network is a multiplicative recurrent neural network.

6. The brain-machine interface system of claim 1, wherein the recurrent neural network is retrained using a second plurality of neural signals.

7. A method for brain-machine interfacing, comprising:
obtaining a plurality of neural signals from a user using at least one multi-electrode array, where:
the plurality of neural signals are obtained over the course of at least two days; and
the plurality of neural signals is modified by randomly adding and removing neural spikes such that the mean number of neural spikes is preserved;
instantiating a recurrent neural network configured to map neural signals to kinematic functions of a prosthetic device;
training the recurrent neural network using the plurality of neural signals;
integrating the trained recurrent neural network into a brain machine interface, where the brain machine interface is in communication with the prosthetic device and the at least one multi-electrode array;
obtaining a neural signal from the user using the at least one multi-electrode array describing an intended movement of the prosthetic device using the at least one multi-electrode array; and
moving the prosthetic device using the trained recurrent neural network to match the intended movement of the user.

8. The method for brain-machine interfacing of claim 7, wherein the prosthetic device is a robotic arm.

9. The method for brain-machine interfacing of claim 7, wherein the prosthetic device is a virtual cursor.

10. The method for brain-machine interfacing of claim 7, wherein the at least one multi-electrode array is implanted into the motor cortex of the user.

11. The method for brain-machine interfacing of claim 7, wherein the recurrent neural network is a multiplicative recurrent neural network.

12. The method for brain-machine interfacing of claim 7, further comprising:
obtaining a second plurality of neural signals; and
retraining the recurrent neural network using the second plurality of neural signals.

13. A method for brain-machine interfacing, comprising:
obtaining a first plurality of neural signals from a user using at least one multi-electrode array on a first day;
obtaining a second plurality of neural signals from the user using the at least one multi-electrode array on a second day;
generating a training data set comprising the first plurality of neural signals and the second plurality of neural signals, where the training data set is modified by randomly adding and removing neural spikes such that the mean number of neural spikes is preserved;
instantiating a recurrent neural network configured to map neural signals from the user to control functions of a prosthetic device;
training the recurrent neural network using the training data set;
integrating the trained recurrent neural network into a brain machine interface, where the brain machine interface is in communication with the prosthetic device and the at least one multi-electrode array;
obtaining a neural signal from the user using the at least one multi-electrode array describing an intended movement of the prosthetic device using the at least one multi-electrode array; and
moving the prosthetic device using the trained recurrent neural network to match the intended movement of the user.

14. The method of claim 13, wherein the control functions are kinematic control functions.

* * * * *